(12) United States Patent
Zhang et al.

(10) Patent No.: US 10,624,604 B2
(45) Date of Patent: Apr. 21, 2020

(54) MEDICAL DIAGNOSTIC HIGH-FREQUENCY X-RAY MACHINES AND POWER SUPPLY DEVICES THEREOF

(71) Applicant: SHENZHEN MINDRAY BIO-MEDICAL ELECTRONICS CO., LTD., Shenzhen (CN)

(72) Inventors: Wan Zhang, Shenzhen (CN); Xuedong Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 690 days.

(21) Appl. No.: 15/293,081

(22) Filed: Oct. 13, 2016

(65) Prior Publication Data

US 2017/0027537 A1 Feb. 2, 2017

Related U.S. Application Data

(63) Continuation of application No. PCT/CN2015/072235, filed on Feb. 4, 2015.

(30) Foreign Application Priority Data

Apr. 17, 2014 (CN) .......................... 2014 1 0156086

(51) Int. Cl.
*A61B 6/00* (2006.01)
*H05G 1/12* (2006.01)

(52) U.S. Cl.
CPC .............. *A61B 6/56* (2013.01); *A61B 6/4405* (2013.01); *H05G 1/12* (2013.01)

(58) Field of Classification Search
CPC .. H02J 5/00; H02J 7/022; H02J 7/345; H05G 1/12
See application file for complete search history.

(56) References Cited

U.S. PATENT DOCUMENTS

| | | | | |
|---|---|---|---|---|
| 4,601,051 A | * | 7/1986 | Santurtun | ................ H05G 1/54 378/105 |
| 5,363,286 A | | 11/1994 | Tsuchiya | |
| 2011/0038190 A1 | * | 2/2011 | Zimpfer | ................... A61B 6/56 363/126 |

(Continued)

FOREIGN PATENT DOCUMENTS

| | | | | |
|---|---|---|---|---|
| CN | 1679378 A | | 10/2005 | |
| CN | 101552348 A | * | 10/2009 | .......... H01M 4/5825 |
| CN | 101552348 A | | 10/2009 | |

(Continued)

*Primary Examiner* — Chih-Cheng Kao
(74) *Attorney, Agent, or Firm* — Kory D. Christensen (57) ABSTRACT

This disclosure relates to medical diagnostic high-frequency X-ray machines and power supply devices thereof. One power supply device can convert an alternating current into a direct current, which is further raised by a boost circuit and stored by a capacitor module, so that the power supply device can provide high voltage and sufficient power to an inverter. Another power supply device can use a lithium iron phosphate battery to power the X-ray machine. Accordingly, the X-ray machine can be lighter, smaller, resistant to high temperature, fast in electrical charging and discharging, and safer, and the usage life of the X-ray machine can be prolonged due to the long cycle life of the lithium iron phosphate battery.

18 Claims, 6 Drawing Sheets

(56) References Cited

U.S. PATENT DOCUMENTS

2012/0027161 A1\* 2/2012 Abenaim ............... A61B 6/027
378/4

FOREIGN PATENT DOCUMENTS

| | | | |
|---|---|---|---|
| CN | 201393172 Y | \* | 1/2010 |
| CN | 201393172 Y | | 1/2010 |
| CN | 102340182 A | | 2/2012 |
| CN | 102570570 A | | 7/2012 |
| CN | 103070693 A | | 5/2013 |
| CN | 103156623 A | | 6/2013 |
| CN | 203523130 U | \* | 4/2014 |
| CN | 203523130 U | | 4/2014 |
| JP | 2010122575 A | | 6/2010 |

\* cited by examiner

MEDICAL DIAGNOSTIC HIGH-FREQUENCY X-RAY MACHINES AND POWER SUPPLY DEVICES THEREOF

CROSS REFERENCE

This disclosure is a continuation of Patent Cooperation Treaty Application No. PCT/CN2015/072235, filed on Feb. 4, 2015, which claims priority and benefits of Chinese Patent Application No. 201410156086.7, filed on Apr. 17, 2014. These applications are hereby incorporated by reference.

TECHNICAL FIELD

This disclosure relates to medical equipment, and specifically to medical diagnostic high-frequency X-ray machines and power supply devices thereof.

BACKGROUND

Medical diagnostic high-frequency X-ray machines (including analog X-ray machines and digital X-ray machines), as for an X-ray radiography diagnostic application in various healthcare organizations, are operated for examining human body parts. X-ray machines can be adapted for various clinical departments, such as orthopedic, ward, emergency room, operating room and ICU (intensive care unit). Accordingly, it is required that the X-ray machines can be movable to improve their availability in those different clinical departments.

Figure 1:
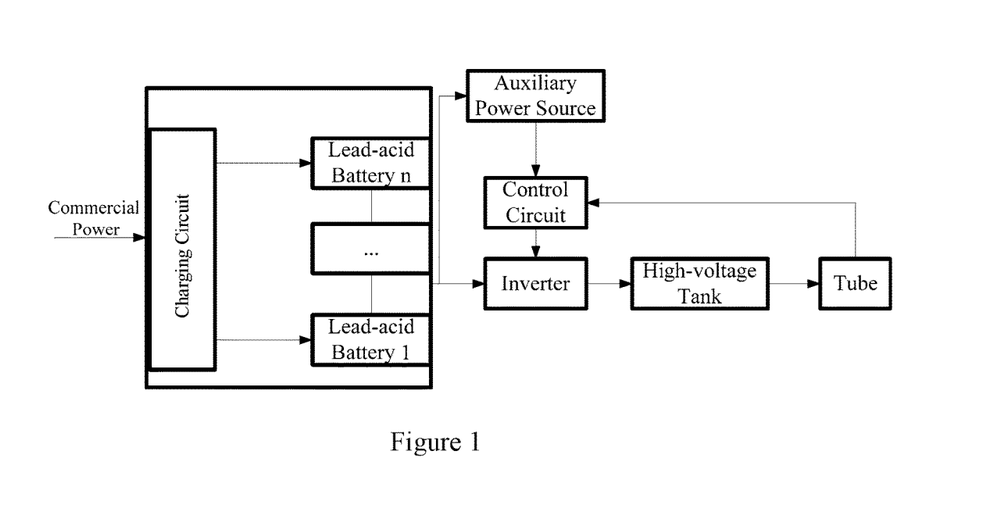
FIG. 1 is a structural diagram for a medical diagnostic high-frequency X-ray machine.

FIG. 1 is a structural diagram for an exposure part of an X-ray machine. An inverter may convert a direct current outputted from a power supply device into a high-frequency (such as 20 kHz) alternating current, which may be inputted into a high-voltage tank. High voltage that is generated by the high-voltage tank or other high-voltage generation device can be inputted into a tube, such that the tube can generate X-rays for radiography. An exposure power for radiography may generally be in a range of 3.5-50 KW. According to this requirement, an input power of the inverter should be at least 15 KW, and an input voltage of the inverter should be at least 300V.

For the digital medical diagnostic high-frequency X-ray machine (which can also be called DR for short), the exposure power for radiography is usually in a range of 3.5-50 KW. However, a maximal output power of a single-phase current of 220V is 2.5 kW, which cannot meet the power demand for DR radiography. Therefore, the DR cannot be directly powered by commercial power, while it can be powered by a battery such as a 12V lead-acid battery.

SUMMARY OF THIS DISCLOSURE

In one aspect, a power supply device for generating high-frequency alternating current is provided in an embodiment. The power supply device can include a direct current power module, at least one power conversion module, and a capacitor module. The direct current power module can include an alternating current-to-direct current converter (AC-DC converter). The AC-DC converter may be connected to commercial power, and convert an alternating current inputted from the commercial power to a first direct current. An output terminal of the AC-DC converter can be connected to an input terminal of the power conversion module to output the first direct current to the power conversion module. The power conversion module can include a boost circuit for boosting a voltage of the first direct current and outputting a second direct current having a predetermined voltage. An output terminal of the boost circuit can be connected to the capacitor module to charge the capacitor module, and an output terminal of the capacitor module can be used as a power output terminal of the power supply device.

In another aspect, a medical diagnostic high-frequency X-ray machine can be provided in an embodiment. The medical diagnostic high-frequency X-ray machine can include the above-described power supply device, an inverter of which an input terminal connects to the capacitor module, a high-voltage generation device, a tube connected to the high-voltage generation device and a control circuit connected to the tube and the inverter respectively. The inverter can obtain the second direct current having the predetermined voltage from the capacitor module, and may invert the second direct current to output a high-frequency alternating current. The high-voltage generation device may receive the high-frequency alternating current and generate a high voltage. The tube can generate X-rays using the high voltage. The control circuit may control, according to an exposure request, the inverter to obtain the second direct current from the capacitor module and to invert the second direct current to output the high-frequency alternating current.

In still another aspect, a medical diagnostic high-frequency X-ray machine can be provided in an embodiment. The medical diagnostic high-frequency X-ray machine can include a power supply device, an inverter, a high-voltage generation device, a tube and a control circuit. The power supply device can include a power source assembly, which may include a lithium iron phosphate battery pack. An input terminal of the inverter can be connected to the power source assembly, where the inverter may obtain a direct current having a predetermined voltage from the power source assembly, and invert the direct current to output a high-frequency alternating current. The high-voltage generation device of which an input terminal connects to the inverter may be used to generate a high voltage. The tube can be connected to the high-voltage generation device and generate X-rays using the high voltage. The control circuit, which connects to the tube and the inverter respectively, can control the inverter according to an exposure request to obtain the direct current from the power source assembly and to invert the direct current to output the high-frequency alternating current.

BRIEF DESCRIPTION OF THE DRAWINGS

The following detailed descriptions of respective embodiments in this disclosure can be understood better when combining with these figures, in which the same structure is represented by the same reference sign. In the figures.

DETAILED DESCRIPTION

For a DR equipment, its exposure power for radiography may be in a range of about 3.5-50 KW. According to an actual power demand of the DR, 15-30 lead-acid batteries of 12V can connect in series to form a battery pack for powering the DR. Under the series-connected configuration, the lead-acid batteries can output a voltage of about 300V, thus meeting an input demand of an inverter. However, this power supply configuration using several lead-acid batteries in series connection has some drawbacks.

First, the total volume and weight of the battery pack are too large. For a mobile DR with an exposure power of 32 KW, the battery pack should have an energy capacity of at least 2000 WH (watt hour) so as to meet one day's radiography needs and movement distance. Here, even if the highest level of lead-acid battery, such as PANASONIC LC-R127R2PG (12V/7.2 AH), is employed, 24 such batteries need to be connected in series to obtain a total capacity of about 2073 WH. Although the total capacity can meet one day's radiography needs and movement distance, the total weight of the battery pack reaches about 60 KG (each battery has a weight of about 2.47 KG), thus causing too large of weight and volume for the DR. The larger the volume and the weight are, the more inconvenient the mobile DR is during the movement.

Second, the battery charge rate is slow. A charge current of a lead-acid battery is about 0.2 C, and thus it takes about 8-10 hours to finish the battery charge. In this case, when the mobile DR is drained off, a quick charge is impossible for the mobile DR using the lead-acid battery configuration. Therefore, this power supply configuration cannot adapt to emergency radiography and movement.

Third, the lead-acid battery is short in cycle life. The lead-acid battery can be used for 300-500 cycles. Provided that the mobile DR needs to go through one charging and one discharging cycle every day, the lead-acid battery may only be used for about one year.

Also, such battery configuration is low in reliability. Fifteen to 30 lead-acid batteries have to be connected in series, so that a high-voltage tank can output a high voltage of at least 125 KV required for radiography, and a power of about 32 KW lasting for at least 100 mS can be met for exposure. Since the lead-acid batteries are connected in series to the supply power, the battery pack needs to provide a current exceeding 89 A. However, when the lead-acid battery operates under a large-current discharge condition of more than about 10 C, its operation reliability will be reduced.

Further, the security of using such power supply configuration cannot be guaranteed. In order to save circuit size and circuit cost, the mobile DR or mobile X-ray apparatus on the market may use a single charger to charge the multiple batteries in series. Hence, those batteries cannot be uniformly charged, where some batteries may be undercharged and some batteries may be overcharged. This may reduce the capacity and the life of the whole battery pack. Even more, when a post-stage circuit of the battery pack is short circuited or when one battery of the battery pack is short circuited, a reverse voltage will be applied across the battery. If the short-circuit failure cannot be eliminated immediately, there will be a serious accident.

In one embodiment of this disclosure, an alternating current provided by a main power can be used to power mobile X-ray machines.

Figure 2:
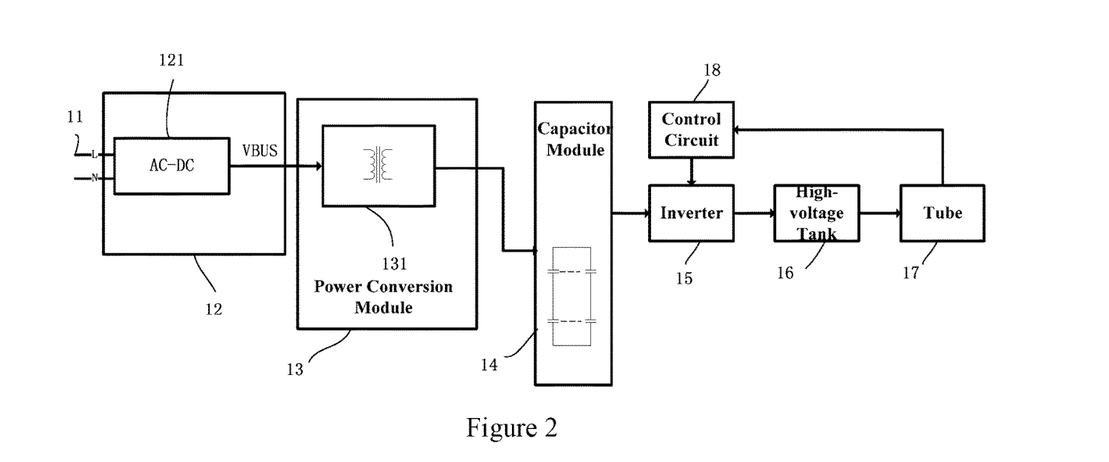
FIG. 2 is a structural diagram for an X-ray machine in an embodiment.

Referring to FIG. 2, a medical diagnostic high-frequency X-ray machine can include a power supply device, an inverter 15, a high-voltage tank 16, a tube 17 and a control circuit 18. The power supply device can include a direct current power module 12, at least one power conversion module 13 and a capacitor module 14.

The direct current power module 12 may include an alternating current-to-direct current converter (AC-DC converter) 121 for AC-DC conversion; that is, the AC-DC converter 121 can convert an inputted alternating current into a first direct current for outputting. In this embodiment, an input terminal of the AC-DC converter 121 can be connected to a main power 11, where the main power can also be called commercial power, and it may be an alternating-current power source of 220V. A single phase of the main power 11 can be an AC power source of 100-240V. Through the conversion of the AC-DC converter 121, a predetermined direct-current operating voltage VBUS can be generated. Some existing AC-DC conversion technology can be used to realize the AC-DC converter 121 according to specific circuit requirements. In some cases, the operating voltage and a power outputted by the AC-DC converter 121 can be in a range of 10-55V and about 1.6 KW. The AC-DC converter can be designed according to specific circuit requirements to output different operating voltages.

An input terminal of the power conversion module 13 may be connected to an output terminal of the AC-DC converter 121 to receive the first direct current from the AC-DC converter 121. The power conversion module 13 can include a boost circuit 131, which may boost a voltage of the first direct current to output a second direct current having a predetermined voltage. In this embodiment, an input terminal of the boost circuit 131 can be connected to the output terminal of the AC-DC converter 121, and an output terminal of the boost circuit 131 can be connected to the capacitor module 14, where the boost circuit 131 can boost the voltage of the direct-current operating voltage VBUS outputted by the AC-DC converter 121. In this embodiment, a high voltage larger than 300V can be obtained by the boost circuit 131, and the capacitor module can be charged using the obtained high voltage. In some embodiments, a high voltage of 680V may be obtained by the boost circuit 131, and an isolation boost circuit may be used as the boost circuit 131 to isolate a low-voltage side from a high-voltage side.

The capacitor module 14, also named as a capacitor box, may be composed of several capacitors that are in series-parallel connection and mounted within one box. In some cases, a switch can be provided in the capacitor box to change the capacitance value. Since the commercial power can only provide the alternating current of 220V and 16 A, its output power cannot reach dozens of kilowatts. In this embodiment, the capacitor module 14 can be used as a power storage of the inverter 15, and the capacitor module 14 can be charged using a voltage of about 300-680V under the boosting operation of the boost circuit 131. If there is no exposure request, the capacitor module 14 can maintain the high voltage and store sufficient energy. If there is the exposure request, the capacitor module 14 can supply power to the inverter 15 and the high-voltage tank 16, so that the tube 17 can be provided with large power for exposure.

An input terminal of the inverter 15 may be connected to the capacitor module 14, and an output terminal of the inverter 15 may be connected to the high-voltage tank 16.

The inverter 15 can obtain an electrical power from the capacitor module 14, and invert the electrical power to output a high-frequency alternating current to the high-voltage tank 16. For instance, a high-frequency electrical power of 20 kHz can be obtained through inversion and outputted to the high-voltage tank 16.

The high-voltage tank 16 as a high-voltage generation device can be used in the X-ray machine having a separated tube-collimator assembly. In some embodiments, the high voltage can alternatively be obtained through other high-voltage generation ways or devices. For instance, the high voltage can be generated by a high-voltage power source in the X-ray machine having a combined tube-collimator assembly.

The tube 17 may be connected to the high-voltage tank and generate X-rays under the action of high voltage.

The control circuit 18, which may be connected to the tube 17 and the inverter 15 respectively, can control the inverter 15 according to the exposure request. The control circuit 18 can control the inverter 15 to obtain the high-voltage direct current from the capacitor module 14, and to invert the high-voltage direct current to output the high-frequency alternating current. Also, the control circuit 18 can be connected to the tube 17, where the voltage and the current outputted by the tube 17 are provided as feedback to the control circuit 18 and compared with a preset voltage (KV) and a preset current (mAs) of the control circuit 18, so that the voltage (KV) and the current (mAs) outputted for exposure by the tube can be controlled and adjusted.

Since the direct current converted from the alternating current cannot provide the X-ray machine with a high-voltage power supply and sufficient energy for exposure, the boost circuit and the capacitor module are included in this embodiment. Through the boosting operation of the boost circuit and the energy storage ability of the capacitor module, there is the high-voltage power supply and the sufficient energy for exposure. Here, when there is a need to expose, the inverter can obtain the electrical power from the capacitor module, and output the high-frequency alternating current after inversion. The electrical power can meet the input demand of the inverter so that the X-ray machine can be powered by the main power.

In another embodiment, a lithium iron phosphate lithium ion battery can be used to replace the lead-acid battery in the X-ray machine. The lithium iron phosphate lithium ion battery, which may also be called a lithium iron phosphate battery, may refer to a lithium ion battery that uses the lithium iron phosphate as an anode material. Each lithium iron phosphate battery can include multiple lithium ion battery units in series-parallel connection. The lithium iron phosphate battery may have some advantages as follows when utilized in the mobile X-ray machine.

1. Compared with the lead-acid battery having the same capacity, the volume and the weight of the lithium iron phosphate battery are approximately one-third of those of the lead-acid battery.

2. The lithium iron phosphate battery can have an extremely long life. The cycle life of a long-life lead-acid battery is around 300 cycles and at most 500 cycles. However, the cycle life of the lithium iron phosphate battery can reach at least 2000 cycles. A cost performance of the lithium iron phosphate battery is more than four times that of the lead-acid battery.

3. The lithium iron phosphate battery will not explode or catch fire even under the most extreme test environment, thus solving the safety risk relative to other lithium batteries.

4. The lithium iron phosphate battery can be quickly charged using a large current.

5. The lithium iron phosphate battery has a broad range of operating temperatures, which can be −20° C. to +75° C., and a peak value under electrical heating of around 350° C. to 500° C. However, the peak value under electrical heating of traditional lithium batteries is about 200° C.

6. The lithium iron phosphate battery is environmentally friendly, since it contains no heavy metals or rare metals. Therefore, the lithium iron phosphate battery is non-toxic and pollution-free during both manufacture and utilization.

Besides such characteristics, the lithium iron phosphate battery has a higher energy density than the lead-acid battery. Thus, when using the lithium iron phosphate battery to replace the lead-acid battery, the X-ray machine can be lighter, smaller, resistant to high temperature, fast in electrical charging and discharging, and safe, and the usage life of the X-ray machine can be prolonged due to the long cycle life of the lithium iron phosphate battery.

The exposure power for radiography is in a range of 3.5-50 KW in the medical diagnostic high-frequency X-ray machine, and thus the input voltage of the inverter is required to be at least 300V. In some embodiments, in order to meet such input requirement of the inverter, several lithium iron phosphate batteries may be connected in series to form a battery pack to meet the voltage requirement. In an example, if the capacity of each lithium iron phosphate battery is about 24V, a dozen lithium iron phosphate batteries need to be connected in series to form the battery pack. In this example, the power supply device may include the power source assembly, which may include a power pack formed by multiple lithium iron phosphate batteries in series. An output terminal of the lithium iron phosphate battery pack may be connected to the input terminal of the inverter, so that the direct current that meets the input voltage requirement of the inverter can be provided to the inverter.

There is still a risk of a short circuit in the series-connected lithium iron phosphate batteries, and a short circuit of the lithium iron phosphate battery may cause an explosion. Accordingly, it may be inappropriate to use the lithium iron phosphate batteries in series, and thus the battery pack including the lithium iron phosphate batteries in series may not directly replace the lead-acid battery pack. In another embodiment, the lithium iron phosphate batteries in parallel connection may be used to power the X-ray machine after a further boosting operation. In this case, the power supply device cannot only provide a high-voltage power supply to the X-ray machine, but it can also provide sufficient energy to the tube of the X-ray machine for exposure.

Figure 3:
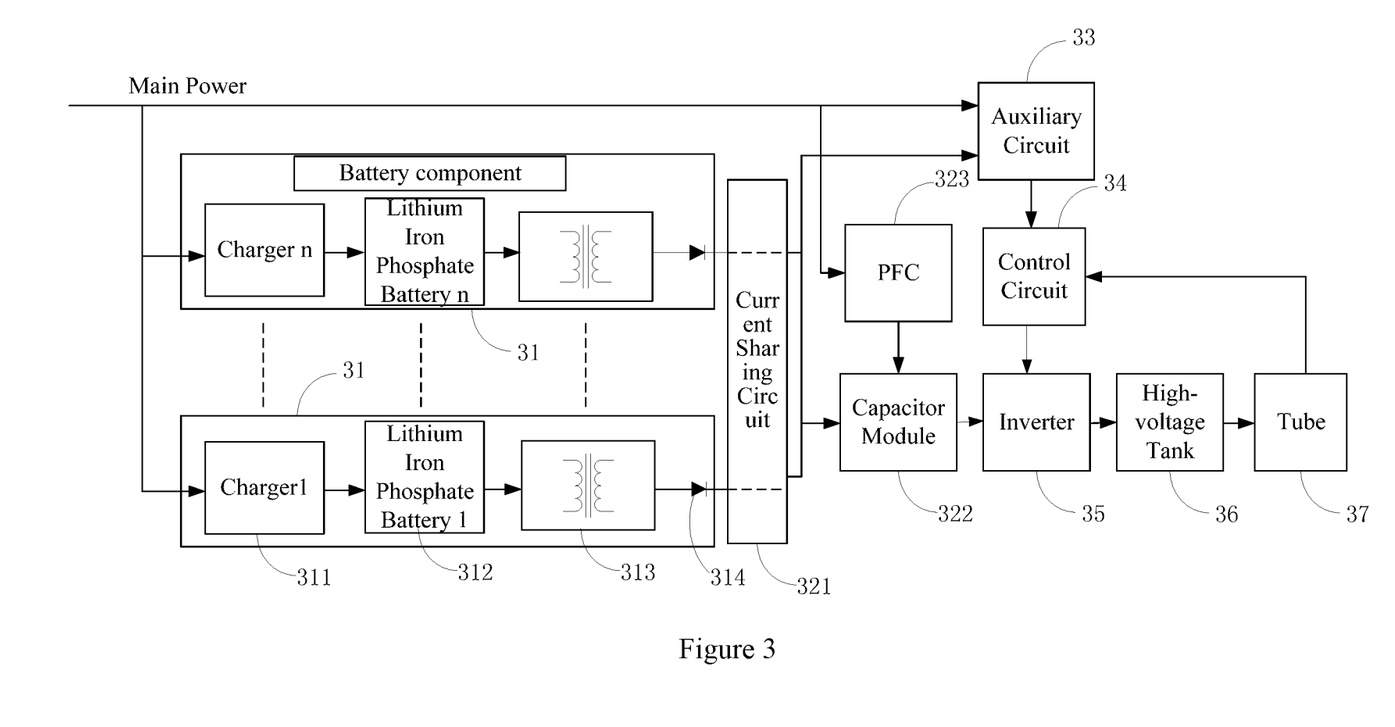
FIG. 3 is a structural diagram for an X-ray machine in an embodiment.

Referring to FIG. 3, the X-ray machine in the embodiment of FIG. 3 can include a power supply device, an auxiliary power source 33, a control circuit 34, an inverter 35, a high-voltage tank 36 and a tube 37, where the power supply device may include a power source assembly 31, a current sharing circuit 321 and a capacitor module 322.

In this embodiment, the power supply device may include n (n is a positive integer) groups of power source assemblies 31 in parallel connection. In some other embodiment, the power supply device can include one group of power source assembly 31.

The power source assembly 31 may include a battery component 312, a charging circuit 311 for charging the battery component 312 and a boost circuit 313, where battery component 312 may be a lithium iron phosphate battery. An input terminal of the charging circuit 311 may be connected to the main power, and an output terminal of the charging circuit 311 may be connected to the battery component 312. An input terminal of the boost circuit 313 may be connected to the battery component 312, and an output terminal of the boost circuit 313 may be connected to the current sharing circuit 321. The boost circuit 313 may raise a voltage of a first direct current outputted by the lithium iron phosphate battery, so as to output a second direct current having a predetermined voltage. In this embodiment, the boost circuit 313 is required to raise the voltage of the direct current outputted by the lithium iron phosphate battery to meet the input requirement of the inverter 35. The voltage outputted from the boost circuit 313 may charge the capacitor module 322. The capacitor module 322 may store the electricity, so as to provide sufficient energy for exposure. In some embodiments, there can be no capacitor module 322, and the multiple lithium iron phosphate batteries in parallel connection can provide sufficient electrical power for exposure. The current sharing circuit 321 may be connected between the boost circuit 313 and the capacitor module 322, and it may perform current sharing on the discharging current of the multiple lithium iron phosphate battery packs.

An input terminal of the auxiliary power source 33 may be connected to the direct current power module or the power conversion module, and an output terminal of the auxiliary power source 33 may be connected to the control circuit 34. The auxiliary power source 33 may convert inputted direct current into the direct current adapted for the control circuit.

When the X-ray machine needs to be charged, the main power (or the commercial power that is an alternating current power supply of 220V) may be connected to the charging circuit 311 of the power source assembly 31 to charge the battery component 312. When the X-ray machine is used to take radiographs of a patient, the power supply device will provide stable direct current power supply, where the auxiliary power source 33 may generate an operating voltage of the control circuit 34, and the capacitor module 322 can serve the inverter 35 as an operating power supply. The control circuit 34 may output control signals to control the inverter 35, the inverter 35 can invert the direct current outputted by the capacitor module into a high-frequency (e.g., about 20 kHz) power supply for outputting to the high-voltage tank 36, the high-voltage tank 36 may generate high voltage that is outputted to the tube 37, and the tube 37 may generate the X-ray for radiographic operation. The control circuit 34 may also output control signals to a collimator (not shown in the figures) and an exposure control device (not shown in the figures), where the collimator can be controlled to adjust a radiographic position of the patient and to set a panel penetrating power (KV) and an X-ray dose (mAs), and the exposure control device can be controlled to perform the exposure operation. Moreover, the voltage and the current outputted from the tube 37 may be provided to the control circuit 34 as a feedback, and compared by the control circuit 34 with a predetermined voltage (KV) and a predetermined current (mAs), so that the voltage (KV) and the current (mAs) outputted for exposure by the tube can be adjusted.

According to the X-ray machines' requirement, 1-n groups of power source assembly(s) can be used in the power supply device. The battery component 312 within each group of power source assembly 31 may be one lithium iron phosphate battery. Each group of power source assembly 31 may be independent from each/one other, where the voltage provided by the battery component 312 may be raised by a same isolation boost circuit 313 before parallel output. In an example, the boost circuit 312 can be a boost transformer, which is not described in detail here. The output terminals of the n groups of power source assemblies 31 can be connected to the current sharing circuit 321, so that the n groups of battery components may discharge uniformly and charge the capacitor module 322 through the current sharing circuit 321. The current sharing circuit 321 may be realized by the following current sharing control methods: an output impedance method, a master-slave configuration method, an automatic current sharing method based on an average current, an automatic current sharing method based on a maximal current, and/or a current sharing control method using an external controller. In an example, the operating current can be lower than 1 C, and the transient large current needed by the X-ray machine may be provided by the capacitor module 322.

In this embodiment, each group of battery component 321 can be provided with a separated charging circuit without interference and/or reliance with each/one other. Based on this circuit configuration, the n groups of battery components 312 can be ensured to charge or discharge uniformly, such that each battery and the whole battery pack can become more reliable.

In this embodiment, each group of battery works independently. In this way, when one battery is in failure, the whole system will not be affected, and no damage will be caused to the other batteries. Accordingly, the battery can be safe in usage based on the circuit configuration.

In some other embodiments, one or more switching devices can be further employed on the basis of the embodiment of FIG. 3, so as to further improve the safety and reliability during usage of the battery. Still as shown in FIG. 3, each group of power source assembly 31 may further include a switching device 314, where the switching device may be connected in series between the boost circuit 313 of the power source assembly 31 and the current sharing circuit 321. In an example, the switching device 314 can be a diode, in which case the circuit is turned on mono-directionally from the direct current power module to the capacitor module 322 and the auxiliary power source, and the current is prevented from backflowing into other groups of power source assemblies when one power source assembly 31 is abnormal.

In some other embodiments, a power factor correction (PFC) module 323 can be provided on the basis of the embodiment of FIG. 3, so that the power supply from the power supply device of the X-ray machine can become more stable.

In some other embodiments, one or more switching devices and a power factor correction (PFC) module can be provided on the basis of the embodiment of FIG. 3, so that the battery can become more safe and reliable, and the power supply from the battery can become more stable. The PFC module may adopt some common PFC techniques, which are not described in detail here.

In those embodiments described above, each lithium iron phosphate battery is configured to work independently from each/one other, and the current sharing control circuit is further adopted to ensure the battery pack discharges uniformly. Also, each battery is charged independently to have uniform charging operation, such that a short circuit of the battery itself or the post-stage circuit can be prevented from causing safety problems, thus improving the safety and reliability of the battery.

In one embodiment, the power supply device can power the X-ray machine using both the alternating current power source and the battery pack.

Figure 4:
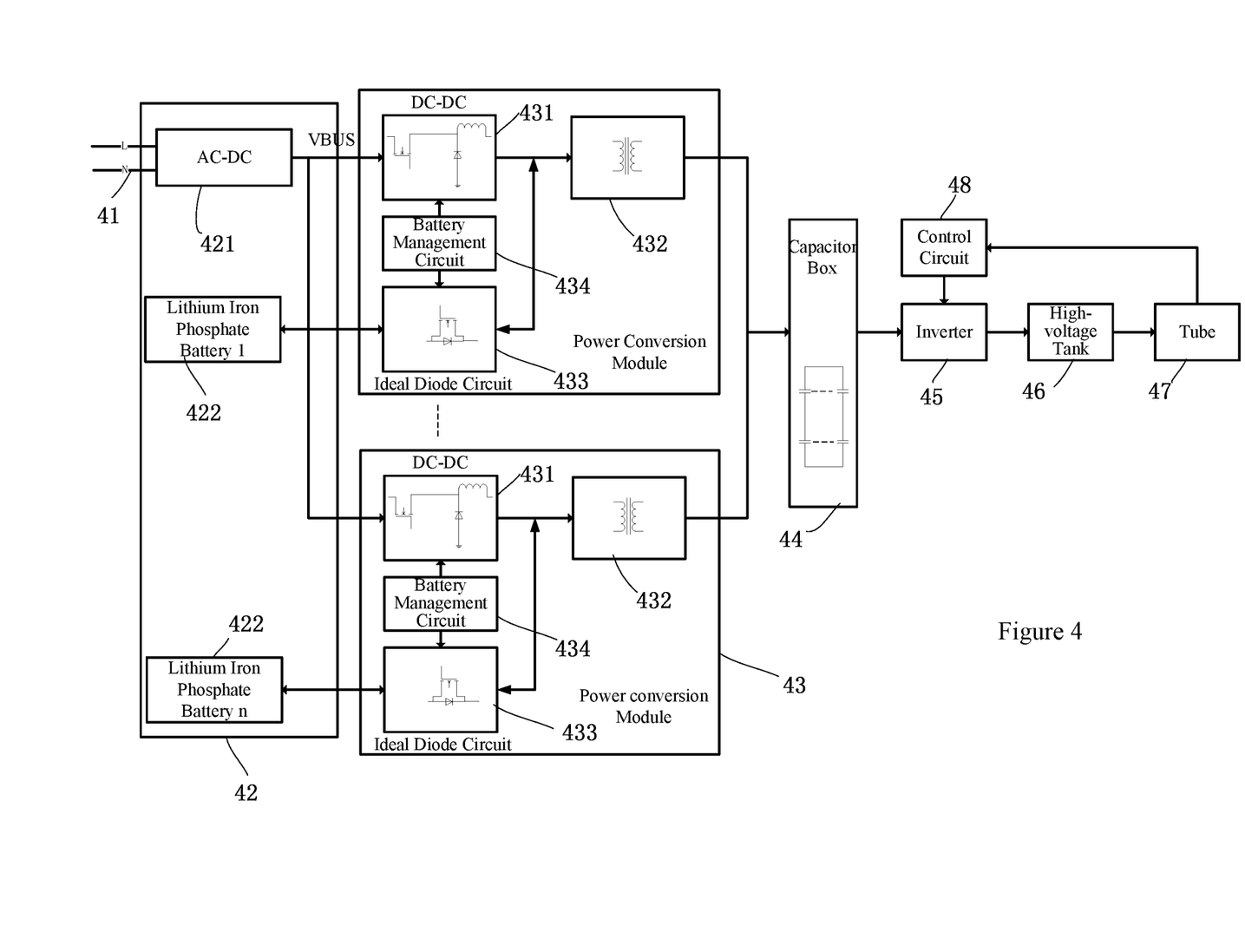
FIG. 4 is a structural diagram for an X-ray machine in an embodiment.

Referring to FIG. 4, the medical diagnostic high-frequency X-ray machine may include a power supply device, an inverter 45, a high-voltage tank 46, a tube 47 and a control circuit 48. The power supply device can include a direct current power module 42, at least one power conversion module 43 and a capacitor module 44.

The direct current power module 42 can include an alternating current-to-direct current (AC-DC) converter 421 and a battery component 422. An input terminal of the AC-DC converter 421 may be connected to a main power 41, and the battery component 422 can be a lithium iron phosphate battery pack. In some other embodiments, the battery component 422 can be other battery packs, such as a lead-acid battery or a lithium battery.

In this embodiment, the battery component 422 may include n groups of lithium iron phosphate battery packs in parallel connection. There can be n power conversion modules, each of which can be connected to one group of lithium iron phosphate battery pack. In some other embodiments, the battery component 422 can be other lithium batteries.

The power conversion module may include a DC-DC conversion circuit 431, a boost circuit 432 and a switching circuit 433. An input terminal of the DC-DC conversion circuit 431 may be connected to an output terminal of the AC-DC converter 421, and the DC-DC conversion circuit 431 can convert the direct current outputted by the AC-DC converter 421 into the direct current that is suitable for charging the battery component 422. The DC-DC conversion circuit 431 may include but is not limited to a BUCK circuit structure, a BOOST circuit structure, and/or a BUCK-BOOST circuit structure. The DC-DC conversion circuit 431 may perform conversion on the direct current outputted by the AC-DC converter 421 through a buck circuit, a boost circuit or a boost-buck circuit, so as to obtain the direct current that is suitable for charging the battery component. An output terminal of the DC-DC conversion circuit 431 may be connected to an input terminal of the boost circuit 432 and the switching circuit 433 respectively. The boost circuit 432 may raise the voltage of the direct current outputted by the DC-DC conversion circuit 431 to a voltage suitable for charging the capacitor module 44. The switching circuit 433 can be connected between the output terminal of the battery component 422, the output terminal of the DC-DC conversion circuit 431 and the input terminal of the boost circuit 432, where the switching circuit 433 can connect the battery component 422 to the DC-DC conversion circuit 431 or connect the battery component 422 to the boost circuit 432.

In this embodiment, the main power 41 may be used in two aspects: one is to provide the operating power to the X-ray machine, and the other one is to charge the battery component 422. When the X-ray machine is connected to the main power 41, the alternating current can be converted into the direct current through the AC-DC converter 421, and the direct current is converted by the DC-DC conversion circuit 431 to be suitable for charging the battery component 422. Here, the direct current after conversion by the DC-DC conversion circuit 431 is raised by the boost circuit 432 to charge the capacitor module 44 on the one hand, and the direct current after conversion by the DC-DC conversion circuit 431 is connected to the battery component 422 through the switching circuit 433 to act as the charging voltage of the battery component 422 on the other hand. When the X-ray machine is disconnected from the main power 41, the switching circuit 433 may connect the battery component 422 to the boost circuit 432, and the battery component 422 may charge the capacitor module 44. In an example, the switching circuit 433 can be controlled by the controller to be switched on or off. For instance, a battery management circuit 434 can be used to control the switching circuit 433, so that the battery component 422 is connected to the DC-DC conversion circuit 431 or the boost circuit 432. Also, the battery management circuit 434 can function as charging protection and current monitoring.

In one embodiment, the switching circuit can be an ideal diode circuit. One terminal of the ideal diode circuit may be connected to the battery pack, and the other terminal of the ideal diode circuit may be connected to the output terminal of the DC-DC conversion circuit or the input terminal of the boost circuit respectively. The ideal diode may have the following characteristics: the ideal diode can be turned on bi-directionally according to preset conditions, and its break-over voltage is small. The ideal diode circuit may refer to the circuit that achieves the function of the ideal diode, while many methods can be used to realize the ideal diode circuit. The ideal diode circuit can be turned on mono-directionally in a selected direction; that is, when a voltage at a first terminal is larger than that at a second terminal in the ideal diode circuit, the ideal diode circuit can be turned on mono-directionally from the first terminal to the second terminal; when the voltage at the first terminal is smaller than that at the second terminal in the ideal diode circuit, the ideal diode circuit can be turned on mono-directionally from the second terminal to the first terminal. In an example, when the X-ray machine is connected to the main power 41, the charging voltage outputted from the DC-DC conversion circuit 431 is larger than that of the battery component 422, and thus the ideal diode circuit is turned on mono-directionally from the DC-DC conversion circuit 431 to the battery component 422. In this situation, the battery component 422 may not supply power to the boost circuit 432. When the X-ray machine is disconnected from the main power 41 and the DC-DC conversion circuit 431 provides no output, the ideal diode circuit may be turned on mono-directionally from the battery component 422 to the boost circuit 432, so that the boost circuit 432 is powered by the battery component 422.

Figure 5:
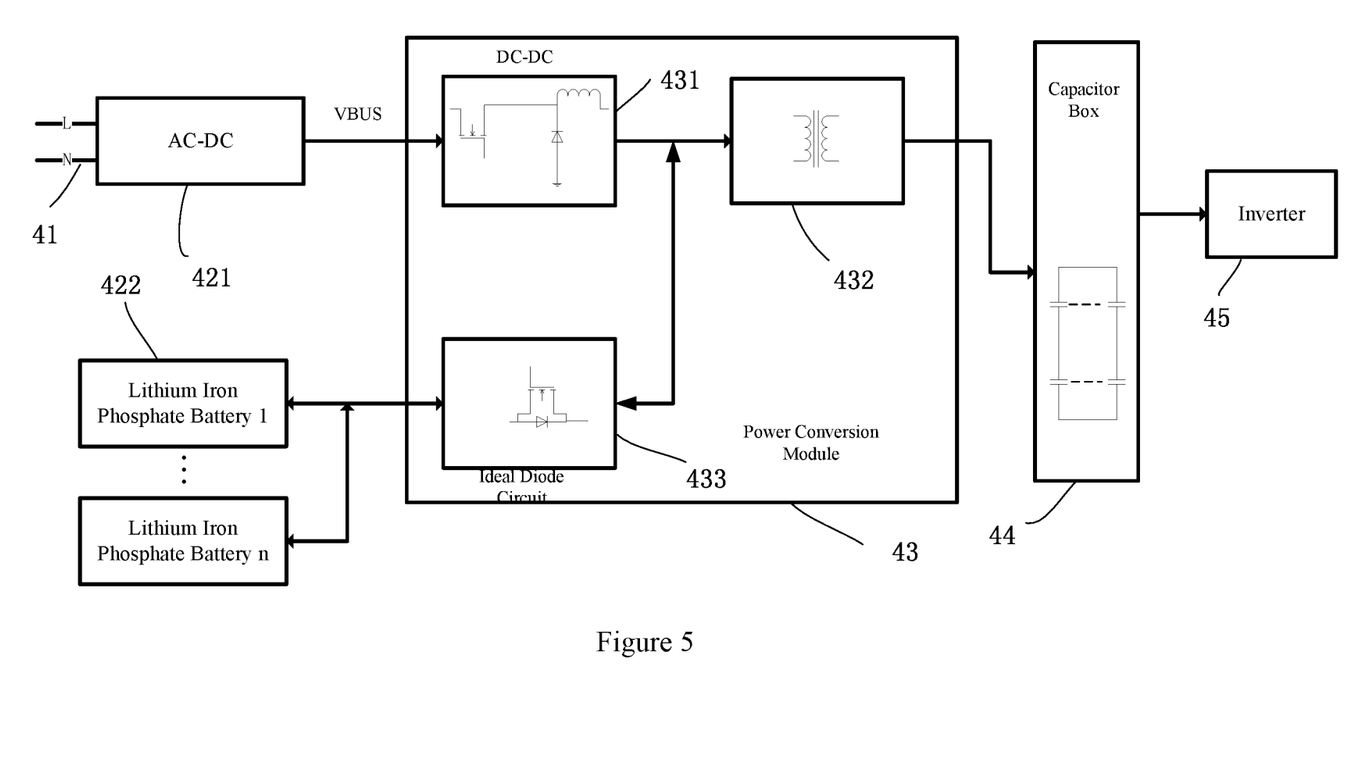
FIG. 5 is a structural diagram for an X-ray machine in an embodiment.
Figure 6:
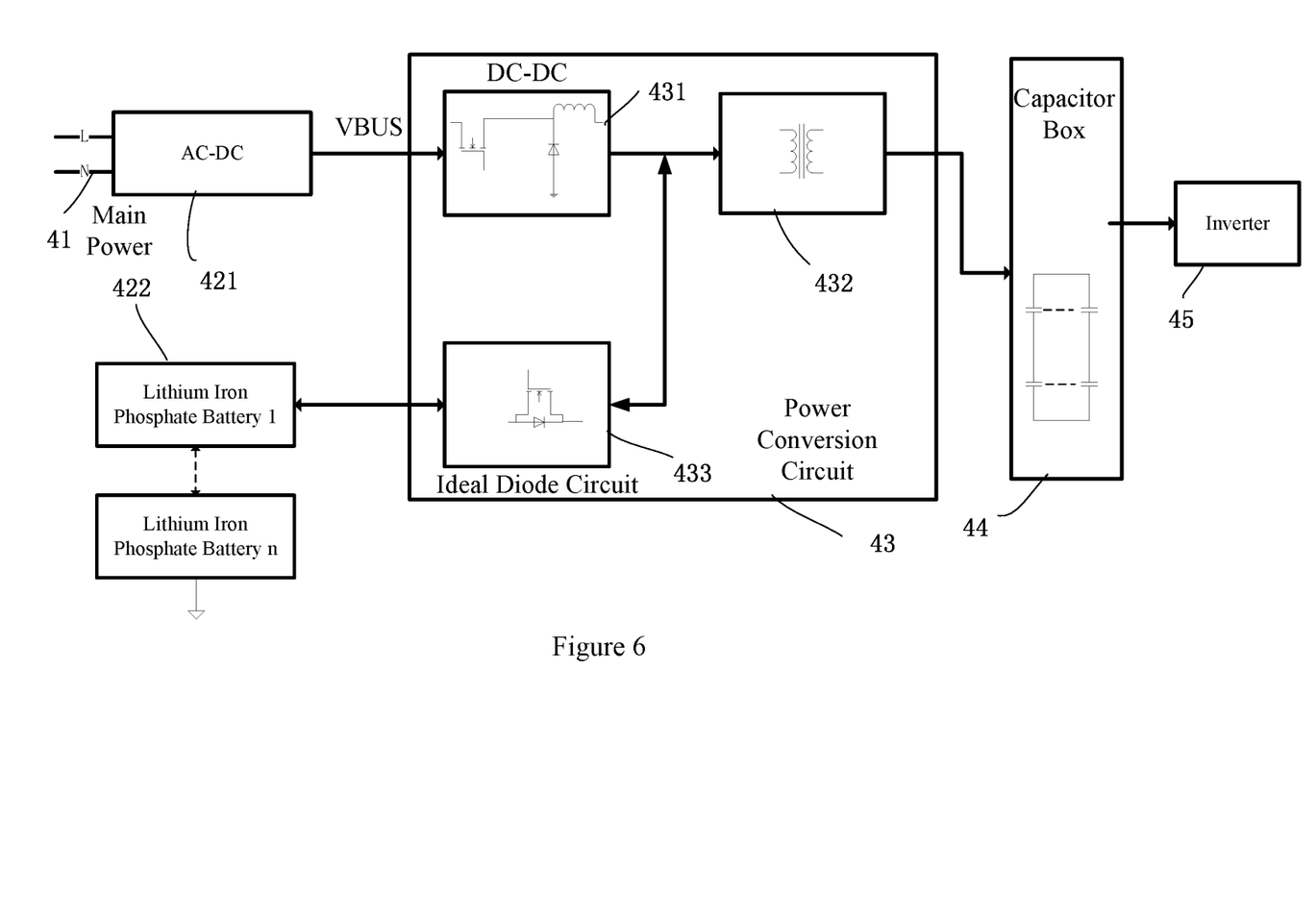
FIG. 6 is a structural diagram for an X-ray machine in an embodiment.

In other embodiments, the battery component 422 may include n groups of battery packs in parallel connection, while there can be one power conversion module. As shown in FIG. 5, a common terminal of the parallel-connected battery packs is connected to the power conversion module, and particularly to one terminal of the switching circuit 433 (e.g., the ideal diode circuit). Besides, the n groups of battery packs can be connected in series before being connected to the power conversion module as shown in FIG. 6.

Two kinds of power sources (i.e., the main power and the battery) can be used to power the X-ray machine. When there is no main power, the X-ray machine can be powered by the battery. When the internal battery is in failure or nearly drained off, the power supply device can power the X-ray machine through the main power. In some cases, it can be set that the X-ray machine is preferred to be powered by the main power.

Sometimes when the alternating current is used as the power source the alternating current may be incapable of providing a power supply that is large enough for the exposure of the X-ray machine (e.g., the X-ray machine may need a large current of about 10 C for exposure). Therefore, it is impossible to make the exposure under a larger current (mAs) by depending only on the alternating current, and the power source may need to be switched from the alternating current to the battery pack. In an embodiment of this disclosure, the ideal diode circuit is used to ensure the large current exposure when the X-ray machine is powered by the alternating current. FIGS. 4-6 illustrate the condition where the alternating current can be used to power the X-ray machine. When the exposure is performed under a large current for the X-ray machine, the output current from the DC-DC conversion circuit 431 to the boost circuit 432 will increase, and the output voltage of the DC-DC conversion circuit 431 will decrease under a rated power. When the output voltage decreases to be lower than that of the battery component 422, the ideal diode circuit may be turned on mono-directionally from the battery component 422 to the boost circuit 432, and the battery component 422 can then power the boost circuit 432. In this case, both the main power and the lithium iron phosphate battery pack can charge the capacitor module 44 simultaneously, so as to provide a larger current exceeding about 320 mAs. After finishing the exposure under the large current, the output voltage of the DC-DC conversion circuit 431 may return, and the ideal diode circuit may return to be turned on mono-directionally from the DC-DC conversion circuit 431 to the battery component 422.

In this embodiment, the battery component can be charged through the DC-DC conversion circuit 431 and the ideal diode circuit. In some other embodiments, the power conversion module can include a charging circuit for charging the battery component. The charging circuit can be connected between the AC-DC converter and the battery component so as to charge the battery component.

Figure 7:
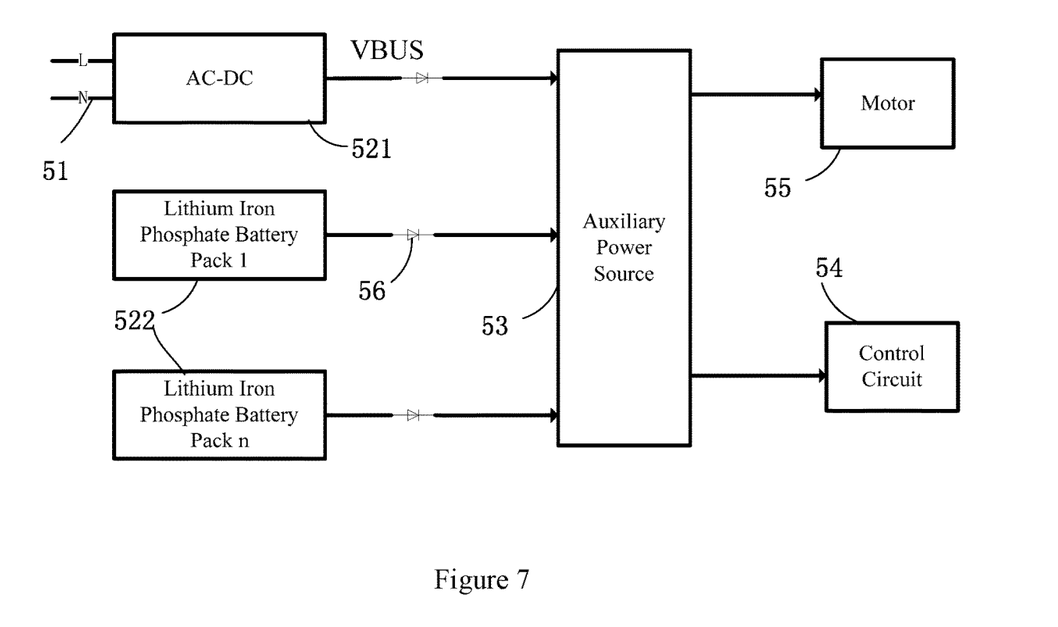
FIG. 7 is a structural diagram for an X-ray machine in an embodiment.

In a mobile medical diagnostic high-frequency X-ray machine, two power sources, i.e., the main power and the battery, can be provided for the exposure and the movement. An input terminal of the auxiliary power source can be connected to the direct current power module or the power conversion module. As shown in FIG. 7, the input terminal of the auxiliary power source 53 may be connected to both the AC-DC converter 521 and the battery component 522, and an output terminal of the auxiliary power source 53 may be connected to both the control circuit 54 and a motor 55. Under this configuration, the inputted direct current can be converted for driving the control circuit 54 and for driving the motor 55 to move respectively, and to be adapted for powering the exposure control circuit. In another embodiment, the auxiliary power source 53 may be connected to both the AC-DC converter 521 and the battery component 522 through an isolation diode 56.

This disclosure is described above as detailed illustrations with reference to specific implementations, while this disclosure should not be limited to these illustrations. For those of ordinary skills in the art, various conclusions or equivalents may be made without departing from the concept of this disclosure, while such conclusions or equivalents should be deemed to be included within the scope of this disclosure.

The invention claimed is:

1. A power supply device for a medical diagnostic high-frequency X-ray machine, comprising:
 a direct current power module that comprises an alternating current-to-direct current converter, the alternating current-to-direct current converter is capable of being connected to a main power, and converting an alternating current inputted from the main power to a first direct current;
 at least one power conversion module, an output terminal of the alternating current-to-direct current converter is connected with an input terminal of the power conversion module to output the first direct current to the power conversion module; the power conversion module comprises a boost circuit that is capable of boosting a voltage of the first direct current and outputting a second direct current having a predetermined voltage; and
 a capacitor module, an output terminal of the boost circuit is connected with the capacitor module to charge the capacitor module, and an output terminal of the capacitor module is a power output terminal of the power supply device;
 wherein the direct current power module further comprises a battery component, and the power conversion module further comprises:
 a DC-DC conversion circuit, an input terminal of the DC-DC conversion circuit is connected with the output terminal of the alternating current-to-direct current converter, and an output terminal of the DC-DC conversion circuit is connected with an input terminal of the boost circuit, wherein the DC-DC conversion circuit is capable of converting the first direct current outputted from the alternating current-to-direct current converter to a third direct current for charging the battery component;
 a switching circuit that is connected between an output terminal of the battery component, the output terminal of the DC-DC conversion circuit and the input terminal of the boost circuit, wherein the switching circuit is capable of connecting the battery component with the DC-DC conversion circuit or connecting the battery component with the boost circuit.

2. The device of claim 1, wherein the switching circuit is an ideal diode circuit; one terminal of the ideal diode circuit connects with the battery component, and the other terminal of the ideal diode circuit connects with the output terminal of the DC-DC conversion circuit or the input terminal of the boost circuit.

3. The device of claim 1, wherein the direct current power module further comprises a battery component that is connected with an input terminal of the boost circuit; the power conversion module further comprises a charging circuit for charging the battery component, wherein the charging circuit is connected between the alternating current-to-direct current converter and the battery component.

4. The device of claim 3, wherein the battery component is a lithium battery pack.

5. The device of claim 4, wherein the lithium battery pack comprises multiple lithium iron phosphate batteries that are connected in parallel; the at least one power conversion module comprises multiple power conversion modules, and each power conversion module connects with one of the lithium iron phosphate batteries.

6. The device of claim 5, wherein each power conversion module further comprises a current sharing circuit and a diode; the current sharing circuit is connected between the boost circuit and the capacitor module, and the diode is connected between the boost circuit and the current sharing circuit; wherein the current sharing circuit is capable of causing the multiple lithium iron phosphate batteries to discharge uniformly.

7. The device of claim 1, wherein the battery component is a lithium battery pack.

8. The device of claim 7, wherein the lithium battery pack comprises multiple lithium iron phosphate batteries that are connected in parallel; the at least one power conversion module comprises multiple power conversion modules, and each power conversion module connects with one of the lithium iron phosphate batteries.

9. The device of claim 8, wherein each power conversion module further comprises a current sharing circuit and a diode; the current sharing circuit is connected between the boost circuit and the capacitor module, and the diode is connected between the boost circuit and the current sharing circuit; wherein the current sharing circuit is capable of causing the multiple lithium iron phosphate batteries to discharge uniformly.

10. A medical diagnostic high-frequency X-ray machine, comprising:
a power supply device that comprises a direct current power module, at least one power conversion module and a capacitor module; the direct current power module comprises an alternating current-to-direct current converter that is capable of being connected to a commercial power, and converting an alternating current outputted from the commercial power to a first direct current; an output terminal of the alternating current-to-direct current converter is connected with an input terminal of the power conversion module to output the first direct current to the power conversion module; the power conversion module comprises a boost circuit that is capable of raising a voltage of the first direct current and outputting a second direct current having a predetermined voltage; an output terminal of the boost circuit is connected with the capacitor module to charge the capacitor module, and an output terminal of the capacitor module is a power output terminal of the power supply device;
an inverter that is connected with the capacitor module, and is capable of obtaining the second direct current from the capacitor module and inverting the second direct current to output a high-frequency alternating current;
a high-voltage generation device for generating a high voltage, an input terminal of the high-voltage generation device connects with the inverter;
a tube that is connected with the high-voltage generation device, and is capable of generating X-ray under the high voltage;
a control circuit that connects with the tube and the inverter respectively, the control circuit is capable of controlling, according to an exposure request, the inverter to obtain the second direct current from the capacitor module and to invert the second direct current to output the high-frequency alternating current;
wherein the direct current power module further comprises a battery component, and the power conversion module further comprises:
a DC-DC conversion circuit, an input terminal of the DC-DC conversion circuit is connected with the output terminal of the alternating current-to-direct current converter, and an output terminal of the DC-DC conversion circuit is connected with an input terminal of the boost circuit, wherein the DC-DC conversion circuit is capable of converting the first direct current outputted from the alternating current-to-direct current converter to a third direct current for charging the battery component;
a switching circuit that is connected between an output terminal of the battery component, the output terminal of the DC-DC conversion circuit and the input terminal of the boost circuit, wherein the switching circuit is capable of connecting the battery component with the DC-DC conversion circuit or connecting the battery component with the boost circuit.

11. The X-ray machine of claim 10, wherein the switching circuit is an ideal diode circuit; one terminal of the ideal diode circuit connects with the battery component, and the other terminal of the ideal diode circuit connects with the output terminal of the DC-DC conversion circuit or the input terminal of the boost circuit.

12. The X-ray machine of claim 10, wherein the direct current power module further comprises a battery component that is connected with an input terminal of the boost circuit; the power conversion module further comprises a charging circuit for charging the battery component, wherein the charging circuit is connected between the alternating current-to-direct current converter and the battery component.

13. The X-ray machine of claim 10, further comprising an auxiliary power source and a motor; an input terminal of the auxiliary power source connects with the direct current power module or the power conversion module, and an output terminal of the auxiliary power source connects with the control circuit and the motor respectively; the auxiliary power source is capable of converting the first or second direct current into a fourth direct current for driving the control circuit and the motor.

14. A medical diagnostic high-frequency X-ray machine, comprising:
a power supply device that comprises a power source assembly, the power source assembly comprises a lithium iron phosphate battery pack; wherein the lithium iron phosphate battery pack comprises multiple lithium iron phosphate batteries that are connected in parallel; the power source assembly further comprises at least one boost circuit of which an input terminal connects with the lithium iron phosphate battery pack, wherein the boost circuit is capable of boosting a first direct current outputted by the lithium iron phosphate battery pack and outputting a second direct current having a predetermined voltage;
an inverter, an input terminal of the inverter is connected with the power source assembly, and the inverter is capable of obtaining the second direct current having the predetermined voltage from the power source assembly and inverting the second direct current to output a high-frequency alternating current;
a high-voltage generation device for receiving the high-frequency alternating current and generating a high voltage;
a tube that is connected with the high-voltage generation device, and is capable of generating X-ray under the high voltage;
a control circuit that connects with the tube and the inverter respectively, the control circuit is capable of controlling, according to an exposure request, the inverter to obtain the second direct current from the power source assembly and to invert the second direct current to output the high-frequency alternating current.

15. The X-ray machine of claim 14, wherein the at least one boost circuit comprises a plurality of the boost circuits, an input terminal of each boost circuit connects with one of the multiple lithium iron phosphate batteries.

16. The X-ray machine of claim 15, wherein the power supply device further comprises a capacitor module; an output terminal of each boost circuit connects with the capacitor module for charging the capacitor module; an output terminal of the capacitor module connects with the input terminal of the inverter.

17. The X-ray machine of claim 16, wherein:
the power supply device further comprises a current sharing circuit that is capable of causing the multiple lithium iron phosphate batteries to discharge uniformly; the current sharing circuit is connected between each boost circuit and the capacitor module;

or the power supply device further comprises a power factor correction module that is powered by a main power and is connected with the capacitor module;

or the power supply device further comprises a current sharing circuit and a diode; the current sharing circuit is connected between each boost circuit and the capacitor module, and the diode is connected between each boost circuit and the current sharing circuit; wherein the current sharing circuit is capable of causing the multiple lithium iron phosphate batteries to discharge uniformly.

18. The X-ray machine of claim 14, wherein the power source assembly further comprises a charging circuit for charging the lithium iron phosphate battery pack; an input terminal of the charging circuit is connected with a main power, and an output terminal of the charging circuit connects with the lithium iron phosphate battery pack.

\* \* \* \* \*